(12) United States Patent
Torrado

(10) Patent No.: US 10,780,109 B1
(45) Date of Patent: Sep. 22, 2020

(54) METHOD FOR TREATING A TOOTH USING SELENITE

(71) Applicant: Laura Torrado, New York, NY (US)

(72) Inventor: Laura Torrado, New York, NY (US)

( * ) Notice: Subject to any disclaimer, the term of this patent is extended or adjusted under 35 U.S.C. 154(b) by 132 days.

(21) Appl. No.: 16/228,868

(22) Filed: Dec. 21, 2018

(51) Int. Cl.
*A61K 33/04* (2006.01)
*A61Q 11/00* (2006.01)
*A61K 31/095* (2006.01)
*A61C 5/00* (2017.01)

(52) U.S. Cl.
CPC .............. *A61K 33/04* (2013.01); *A61Q 11/00* (2013.01); *A61C 5/00* (2013.01); *A61K 31/095* (2013.01)

(58) Field of Classification Search
CPC ........ A61C 5/00; A61K 33/04; A61K 31/095; A61Q 11/00
USPC .......................................... 433/226
See application file for complete search history.

(56) References Cited

U.S. PATENT DOCUMENTS

| | | | |
|---|---|---|---|
| 2,494,403 A | 1/1950 | Nies et al. | |
| 4,604,142 A | 8/1986 | Kamohara et al. | |
| 4,647,311 A | 3/1987 | Ohi et al. | |
| 5,505,771 A | 4/1996 | Chihara et al. | |
| 5,685,356 A | 11/1997 | Kubo et al. | |
| 5,718,749 A * | 2/1998 | Horiuchi ................. | C04B 28/14 106/38.35 |
| 6,881,258 B2 | 4/2005 | Delee et al. | |
| 7,850,996 B2 | 12/2010 | Kossler et al. | |
| 8,382,478 B2 | 2/2013 | White | |
| 9,169,160 B2 * | 10/2015 | Ichino ..................... | C04B 28/14 |
| 9,198,837 B2 * | 12/2015 | Mori ........................ | A61K 6/76 |
| 9,408,783 B2 * | 8/2016 | Mori ...................... | A61K 6/858 |

FOREIGN PATENT DOCUMENTS

CN 101766542 B * 9/2011
KR 20060029562 A * 4/2006

* cited by examiner

*Primary Examiner* — Matthew M Nelson
(74) *Attorney, Agent, or Firm* — Michael J. Feigin, Esq.; Feigin and Fridman LLC

(57) ABSTRACT

A method of treating a tooth of a user. Initially, a tooth is cut to have an opening of at least 1 to 4 mm in the direction along an occlusal surface of the tooth, or a tooth already cut to have such an opening is located. Following ensuring that the opening is dry, powdered selenite is inserted into the opening. Subsequently, the powdered selenite is covered with a dental composite, thereby sealing the powdered selenite in the tooth.

15 Claims, 5 Drawing Sheets

METHOD FOR TREATING A TOOTH USING SELENITE

FIELD OF THE DISCLOSURE

The disclosed technology relates to a method of treating teeth, and, more specifically, to a method of treating a tooth by insertion of powdered selenite thereinto.

BACKGROUND

Selenite is $CaSO_4.2H_2O$ Selenite and found in gypsum rock. Some use it for it's "metaphysical" properties. Proposed herein is another use for same.

SUMMARY OF THE DISCLOSED TECHNOLOGY

The disclosed technology described herein addresses a need, unfulfilled in the prior art, for providing a method for treating a tooth of a user by insertion of powdered selenite thereinto. The method includes cutting a tooth to have an opening, or locating an already cut tooth having an opening, the opening having a length of at least 2 to 5 mm in at least one direction along an occlusal surface of the tooth. In next steps of the method, the opening is ensured to be dry, and powdered selenite is inserted into the opening. Subsequently, the powdered selenite is covered with a dental composite sealing the powdered selenite in the tooth.

In some embodiments, the opening has a depth in the range of 5 to 10 mm

In some embodiments, ensuring that the opening is dry includes inserting an absorbent material, such as cotton roll, into the mouth of the user for absorption of water therein before the step of inserting selenite, particularly when the selenite is water soluble.

In some embodiments, cutting the tooth, or locating an already cut tooth, includes cutting a dental crown or locating an already cut dental crown. Similarly, cutting the tooth may include cutting a dental inlay, a dental onlay, or a dental overlay, and or locating an already cut tooth may include locating an already cut dental inlay, dental onlay, or dental overlay.

In some embodiments, the tooth being cut, or the tooth located to already be cut, forms part of a denture. The denture may be a fixed denture or a removable denture. Similarly, the tooth being cut, or the tooth located to already be cut, may form part of a dental bridge, or of any other restorative dental structure inserted in the mouth of the user, or adapted to be inserted in the mouth of the user.

In some embodiments, the cut tooth or the already cut tooth is an implanted tooth.

In some embodiments, when the powdered selenite is inserted into the opening, a volume of powdered selenite in the range of 1 to 2 gr is inserted. In some embodiments, when the powdered selenite is inserted into the opening, a weight of powdered selenite in the range of 1 to 3 grm is inserted.

DETAILED DESCRIPTION OF EMBODIMENTS OF THE DISCLOSED TECHNOLOGY

The presently disclosed technology is directed towards a method for treating a tooth by inserting powdered selenite into the tooth, and sealing the powdered selenite therein.

Figure 1A:
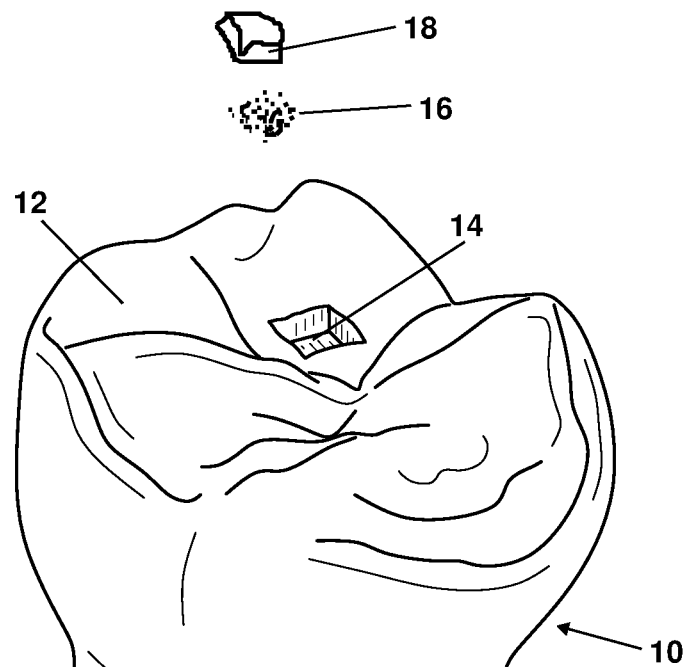
FIGS. 1A and 1B respectively show a perspective view and an occlusal planar view of a tooth treated in accordance with an embodiment of a method of the disclosed technology.
Figure 1B:
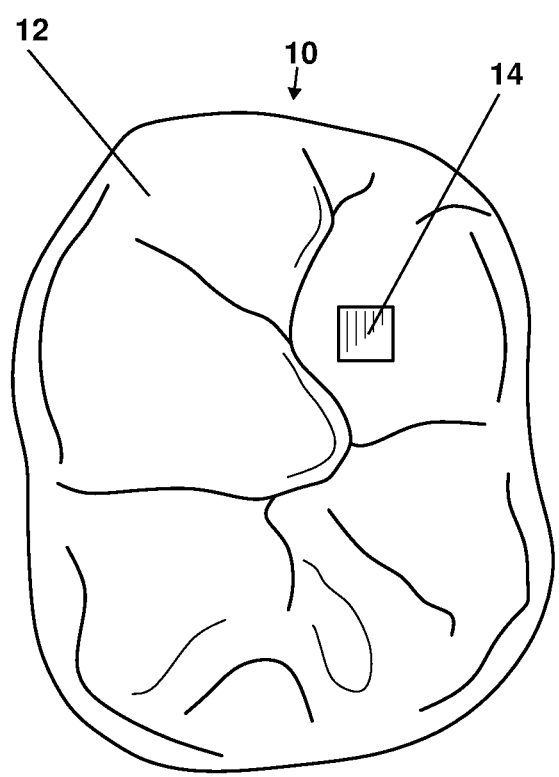

FIGS. 1A and 1B respectively show a perspective view and an occlusal planar view of a tooth 10 treated in accordance with an embodiment of a method of the disclosed technology. As seen in FIGS. 1A and 1B, the occlusal surface 12 of the tooth 10 is cut to have an opening 14.

In some embodiments, opening 14 has a depth in the range of 3 mm. In some embodiments, in at least one dimension thereof, opening 14 has a length in the range of 1 mm to 4 mm (millimeter). In some embodiments, opening 14 has a length in the range of 1 mm to 4 mm in two orthogonal directions. For example, opening 14 may be a square opening, where each side of the square has a length in the range of 1 mm to 4 mm. In other embodiments, opening 14 may be a generally circular opening having a diameter in the range 1 mm to 5 mm.

In some embodiments, the user may already have a tooth including an opening as described herein, for example a tooth that has previously been cut to include such an opening. In such embodiments, there is no need to cut another opening in the user's tooth, and the existing opening may be used.

Following cutting of opening 14 in tooth 10, or identifying a tooth with a pre-existing or pre-cut opening, it is ensured that the opening is dry. In some embodiments, this includes using an absorbent material, such as cotton rolls, for absorption of water in the mouth of the user.

Powdered selenite 16 is then inserted into opening 14 in the tooth. In some embodiments, the powdered selenite is water soluble. In some embodiments, the volume of powdered selenite inserted into opening 14 is in the range of 2 to 4 grams. In some embodiments, the weight of powdered selenite inserted into opening 14 is in the range of 2 to 4 grams Following insertion of the powdered selenite 16 into opening 14, the selenite is covered with a dental composite 18, a resin based matrix composed of a bisphenol A-glycidyl methacrylate or urethane dimethacrylate or a crystalline polyceramic matrix filled with and inorganic filler like silicon dioxide. such, thereby sealing the powdered selenite 16 within opening 14. In some embodiments, the dental composite 18 fills the entirety of opening 14. In some embodiments, an upper surface of the dental composite 18 is shaped to match a contour of the occlusal surface of the tooth, prior to cutting opening 14 therein.

Figure 2:
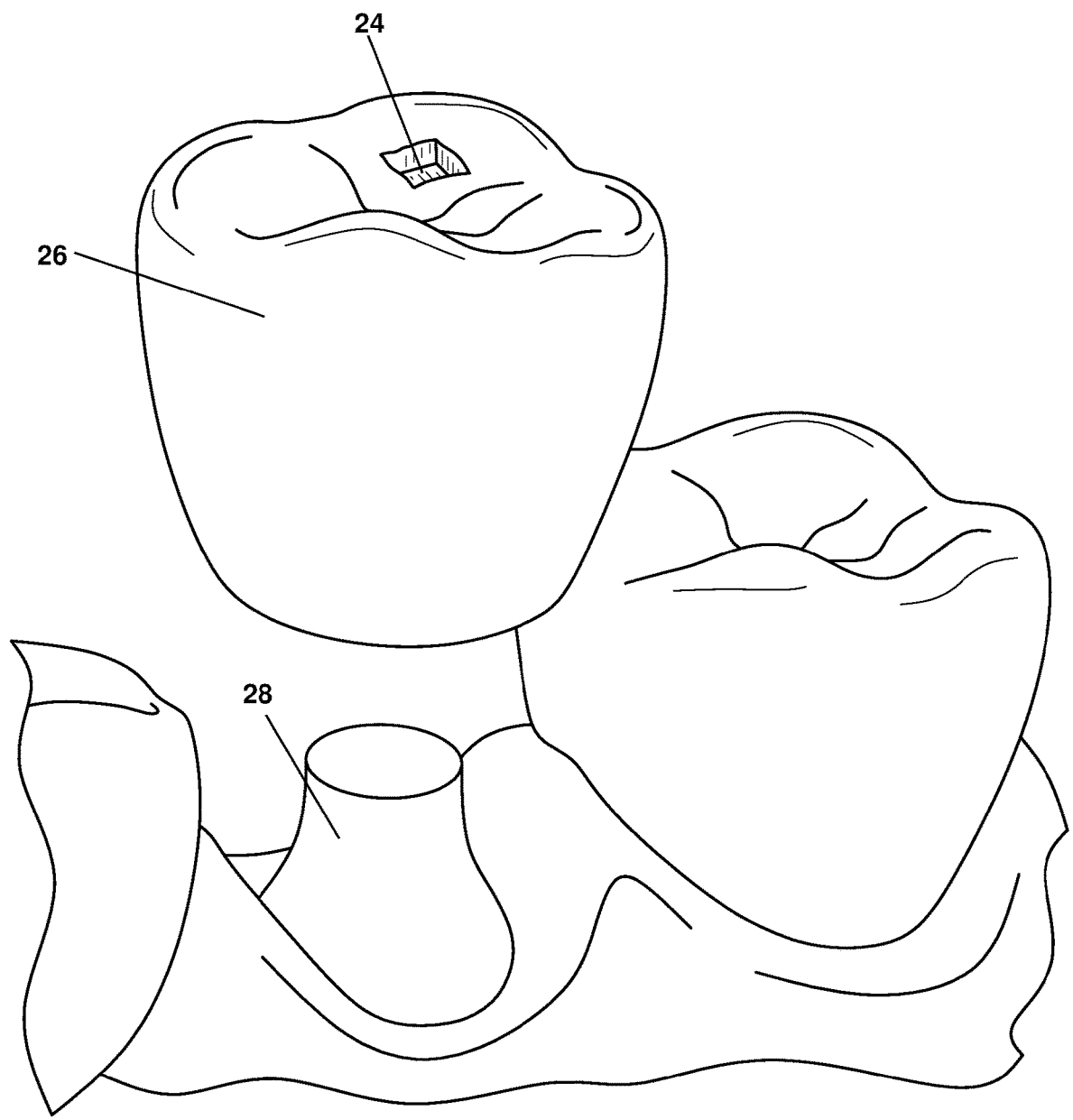
FIG. 2 is a perspective view of a dental crown treated in accordance with an embodiment of a method of the disclosed technology.

Turning to FIG. 2, it is seen that an opening 24 as similar to opening 14 of FIGS. 1A and 1B is formed in a dental crown 26, adapted to be mounted on a tooth base 28 in the user's mouth. The opening 24 is adapted to be filled with powdered selenite and then sealed, as described hereinabove with respect to FIGS. 1A and 1B.

Figure 3A:
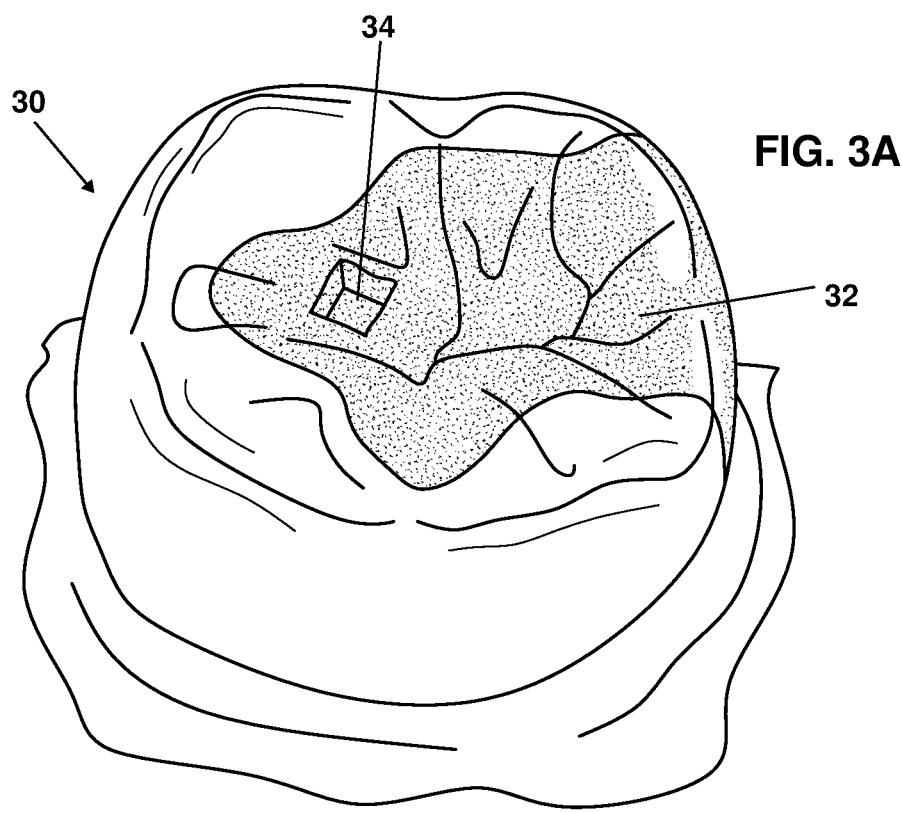
FIGS. 3A and 3B are perspective view illustrations of a tooth treated in accordance with an embodiment of a method of the present invention, the tooth having a porcelain inlay and a porcelain onlay, respectively.

FIG. 3A illustrates a tooth 30 having a porcelain inlay 32 therein. An opening 34 similar to opening 14 of FIGS. 1A and 1B is formed in the porcelain inlay 32. The opening 34 is adapted to be filled with powdered selenite and sealed, as described hereinabove with respect to FIGS. 1A and 1B.

Figure 3B:
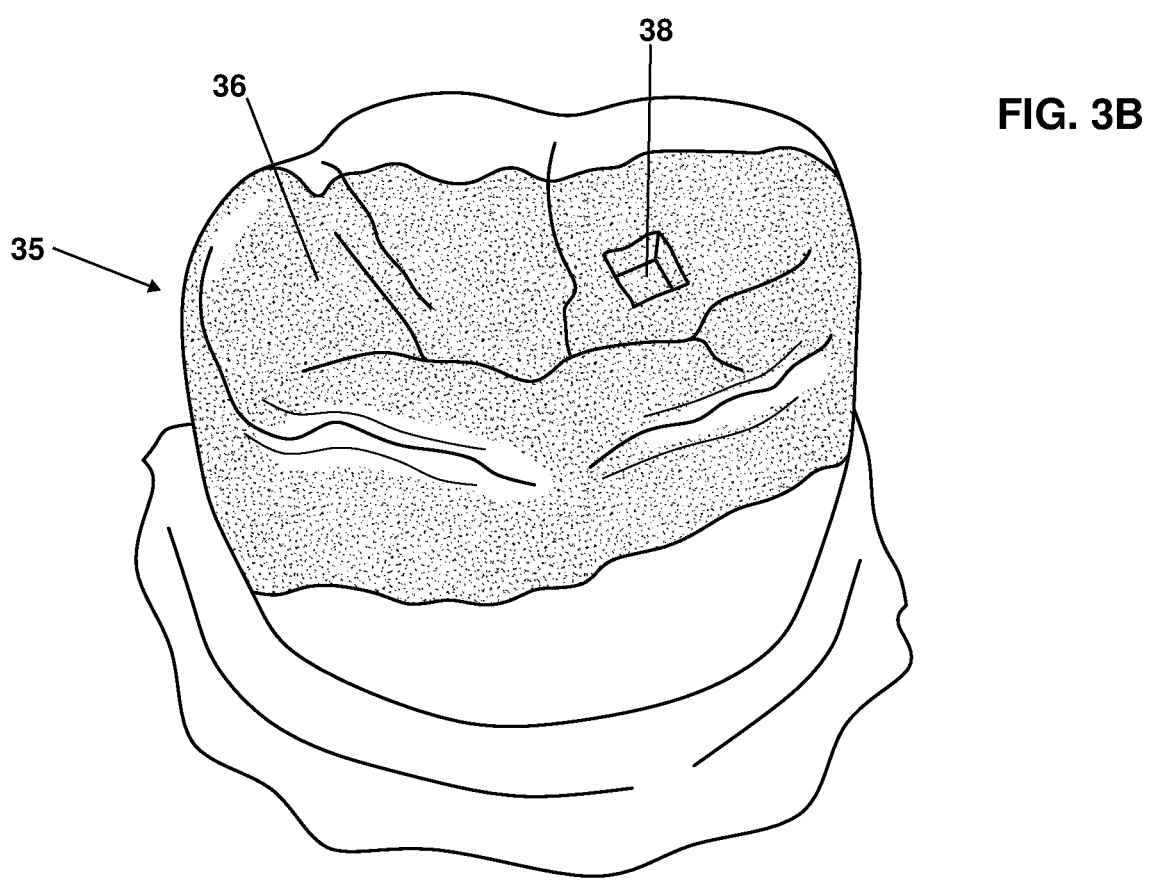

FIG. 3B illustrates a tooth 35 having a porcelain onlay 36 therein. An opening 38 similar to opening 14 of FIGS. 1A and 1B is formed in the porcelain onlay 36. The opening 38 is adapted to be filled with powdered selenite and sealed, as described hereinabove with respect to FIGS. 1A and 1B.

Figure 4:
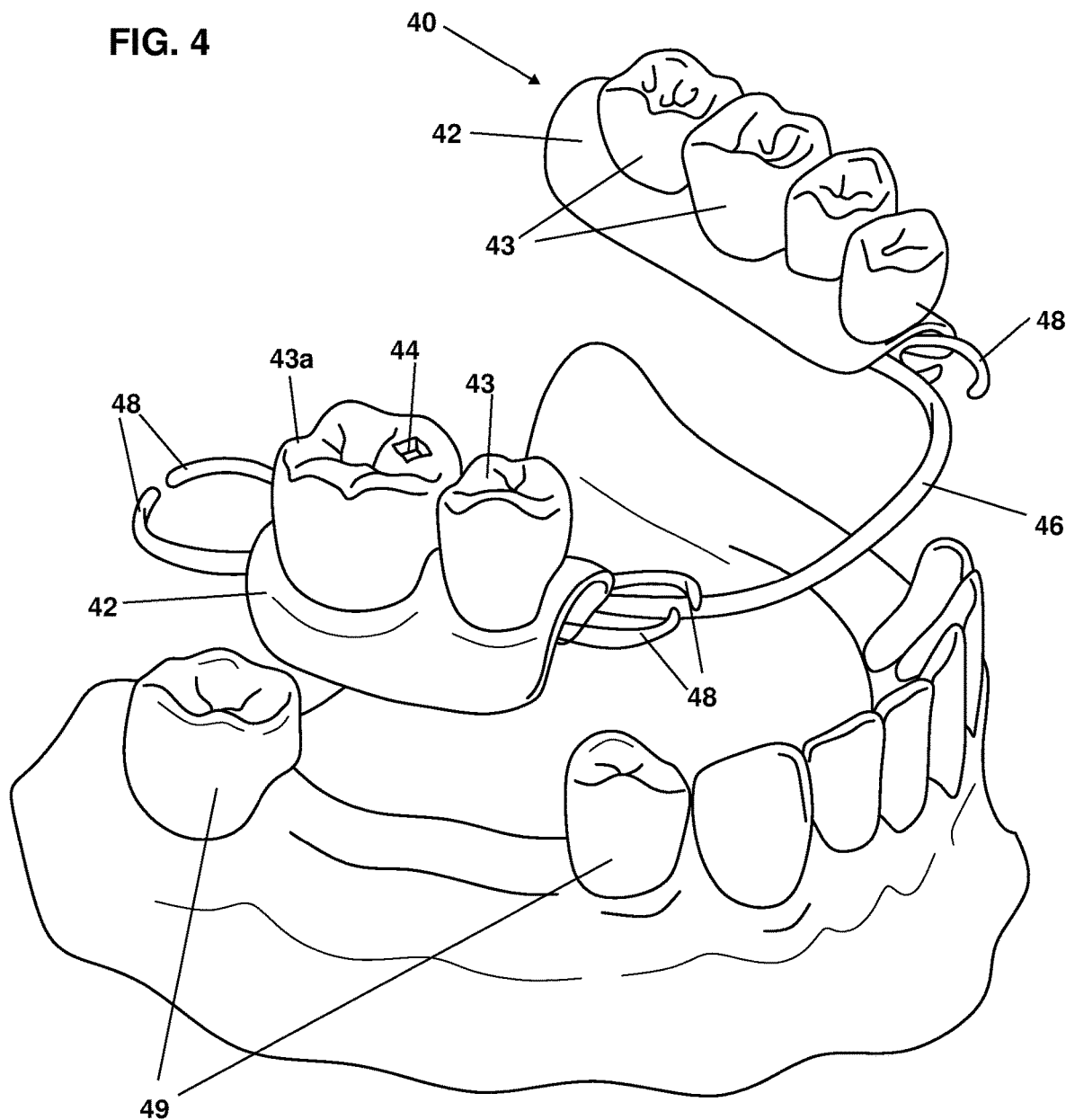
FIG. 4 is a perspective view illustration of artificial teeth on a partial denture adapted to engage healthy teeth in the user's mouth, one of the teeth of the denture being treated in accordance with an embodiment of the method of the disclosed technology.

FIG. 4 shows a partial denture 40 including two base portions 42, having mounted thereon a plurality of artificial teeth 43. One of the plurality of artificial teeth, artificial tooth 43a, is cut to include an opening 44, similar to opening 14 described hereinabove with respect to FIGS. 1A and 1B. The opening 44 is adapted to be filled with powdered selenite and sealed, as described hereinabove with respect to FIGS. 1A and 1B. Base portions 42 are mounted on a wire frame 46, which includes wire appendages 48 for fixing of the denture to healthy teeth 49 in the user's mouth.

It will be appreciated by those of skill in the art, that though FIG. 4 illustrates partial dentures, adapted to be fixedly attached to the user's teeth, the method of the disclosed technology is equally applicable to full dentures adapted to be placed over the whole gum of the user, and to removable dentures.

Figure 5:
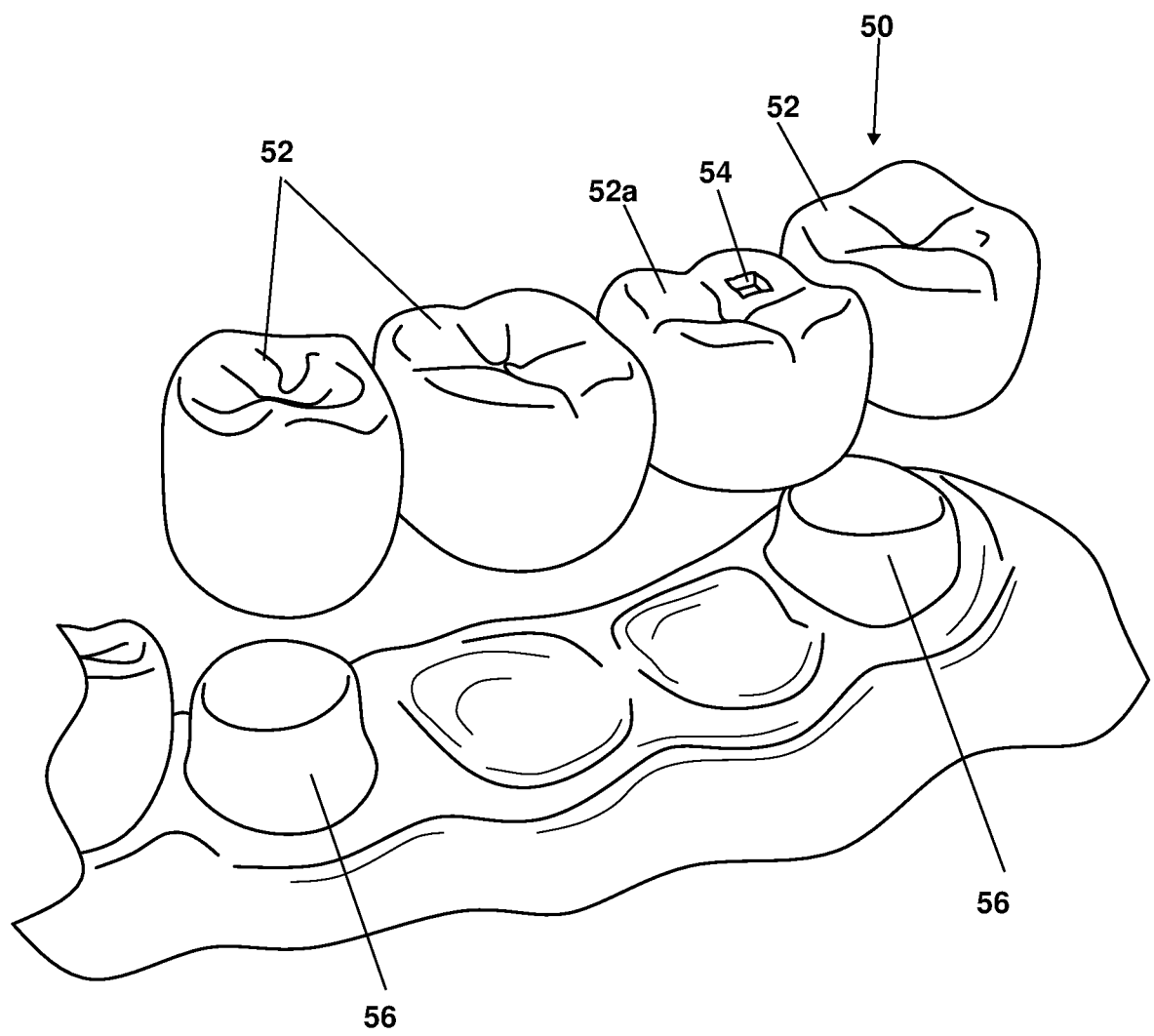
FIG. 5 is a perspective view illustration of artificial teeth on a bridge adapted to be mounted on a user's gums, one of the teeth of the bridge being treated in accordance with an embodiment of the method of the disclosed technology.

FIG. 5 shows a partial dental bridge 50 including a plurality of artificial teeth 52, which are typically connected to one another using meal wiring (not explicitly shown). One of the plurality of artificial teeth, artificial tooth 52a, is cut to include an opening 54, similar to opening 14 described hereinabove with respect to FIGS. 1A and 1B. The opening 54 is adapted to be filled with powdered selenite and sealed, as described hereinabove with respect to FIGS. 1A and 1B. Bridge 50 is adapted to be mounted onto tooth bases (or implanted bases) 56 in the user's mouth.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described herein above are also contemplated and within the scope of the invention.

I claim:

1. A method of treating a tooth of a user, the method comprising the steps of:

cutting a tooth to have an opening, or locating an already cut tooth having an opening, said opening having a length of at least 0.5 mm to 1 millimeter in at least one direction along an occlusal surface of said tooth;

ensuring said opening is dry;

inserting powdered selenite into said opening;

covering said powdered selenite with a dental composite sealing said powdered selenite in said tooth.

2. The method of claim 1, where said ensuring said opening is dry includes inserting an absorbent material into a mouth of the user for absorption of water therein before said step of inserting selenite, wherein said selenite is water soluble.

3. The method of claim 1, wherein said cutting a tooth or locating an already cut tooth comprises cutting a dental crown or locating an already cut dental crown.

4. The method of claim 1, wherein said cutting a tooth or locating an already cut tooth comprises cutting a dental inlay or locating an already cut dental inlay.

5. The method of claim 1, wherein said cutting a tooth or locating an already cut tooth comprises cutting a dental onlay or locating an already cut dental onlay.

6. The method of claim 1, wherein said cutting a tooth or locating an already cut tooth comprises cutting a dental overlay or locating an already cut dental overlay.

7. The method of claim 1, wherein said cutting a tooth or locating an already cut tooth comprises cutting a tooth forming part of a denture or locating an already cut tooth forming part of a denture.

8. The method of claim 7, wherein said denture is a removable denture.

9. The method of claim 7, wherein said denture is a fixed denture.

10. The method of claim 1, wherein said cutting a tooth or locating an already cut tooth comprises cutting a tooth forming part of a dental bridge or locating an already cut tooth forming part of a dental bridge.

11. The method of claim 1, wherein said cutting a tooth or locating an already cut tooth comprises cutting an implanted tooth or locating an already cut implanted tooth.

12. The method of claim 1, wherein said cutting a tooth or locating an already cut tooth comprises cutting a tooth forming part of a restorative dental structure adapted to be inserted in the mouth of the user, or locating an already cut tooth forming part of a restorative dental structure inserted in the mouth of the user.

13. The method of claim 1, wherein said inserting said powdered selenite into said opening comprises inserting a volume of powdered selenite in the range of 2 to 4 grams.

14. The method of claim 1, wherein said inserting said powdered selenite into said opening comprises inserting a quantity of powdered selenite having a weight in the range of 2 to 4 grams.

15. The method of claim 1, wherein said opening has a depth in the range of 2 to 5 mm.

* * * * *